United States Patent [19]
Caddy et al.

[11] Patent Number: 5,969,129
[45] Date of Patent: *Oct. 19, 1999

[54] PURIFICATION OF POLYNUCLEOTIDES FROM POLYNUCLEOTIDE/POLYSACCHARIDE MIXTURES

[75] Inventors: Brian Caddy, Torrance, United Kingdom; Jing Cheng, Philadelphia, Pa.

[73] Assignee: The University of Strathclyde, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/682,573

[22] PCT Filed: Jan. 26, 1995

[86] PCT No.: PCT/GB95/00150

§ 371 Date: Aug. 26, 1996

§ 102(e) Date: Aug. 26, 1996

[87] PCT Pub. No.: WO95/20594

PCT Pub. Date: Aug. 3, 1995

[30] Foreign Application Priority Data

Jan. 27, 1994 [GB] United Kingdom .................. 9401603

[51] Int. Cl.$^6$ .............................. C12P 19/34; C07H 1/02; C07H 21/00
[52] U.S. Cl. .................... 536/25.4; 435/91.1; 536/25.41; 536/25.42; 935/19; 935/20; 935/21
[58] Field of Search ............................. 536/25.4, 25.41, 536/25.42; 435/91.1; 935/19, 20, 21

[56] References Cited

FOREIGN PATENT DOCUMENTS

| | | |
|---|---|---|
| 0 158 148 | 10/1985 | European Pat. Off. . |
| 0 284 959 | 10/1988 | European Pat. Off. . |
| 2 229 208 | 6/1972 | Germany . |
| 1 392 417 | 4/1975 | United Kingdom . |

OTHER PUBLICATIONS

1993 Bio–Rad Lite Science Research Products Catalog, p. 23., Hercules, CA. 94547.

N. Do and R.P. Adams, "A Simple Technique for Removing Plant Polysaccharide Contaminants from DNA" *Biotechniques* 10 No. 2, 162–166 (1991).

B.J.B. Johnson, Synthesis of a Nitrobenzeneboronic Acid Substituted Polyacrylamide and Its Use in Purifying Isoaccepting Transfer Ribonucleic Acids; *Biochemistry*, 20, 6103–6108, (1981).

R.E. Duncan and P.T. Gilham; Isolation of Transfer RNA Isoacceptors by Chromatography on Dihydroxboryl–Substituted Cellulose, Polyacrylamide, and Glass; *Analytical Biochemistry* 66, 532–539, (1975).

Database WPI, Derwent Publications Ltd., London, GB; AN 92–311774 & JP, A,04 216 459 (Nippon Oils), Aug. 6, 1992 see abstract.

Database WPI, Derwent Publications Ltd., London, GB; AN 80–47004C & JP, A,55 066 525 (Nippon Corn Starch), May 21, 1980 see abstract.

B. Rether et al; Isolation of Polysaccharide–Free DNA from Plants; *Plant Molecular Biology Reporter* 11, 333–337 (1993).

*Primary Examiner*—Gary L. Kunz
*Attorney, Agent, or Firm*—Alston & Bird LLP

[57] ABSTRACT

A process for isolating polynucleotides from aqueous mixtures containing both polynucleotides and polysaccharides is described. The process uses polymer gels containing —B(OH)$_2$ groups, and is useful in purifying deoxyribonucleic acid extracted from plants.

17 Claims, No Drawings

PURIFICATION OF POLYNUCLEOTIDES FROM POLYNUCLEOTIDE/POLYSACCHARIDE MIXTURES

FIELD OF INVENTION

The present invention relates to the isolation of polynucleotides from an aqueous mixture containing the polynucleotides and polysaccharides, particularly to the purification of deoxyribonucleic acid (DNA) extracted from plants.

BACKGROUND

Co-pending patent application WO92/05181 herein incorporated by reference discloses the purification of polynucleotides (particularly DNA) derived from human or animal cells by the removal of protein impurities. The proteins are removed by reaction with a cross-linked silica gel material having free CHO or CO groups, so as to remove the proteins as a solid or semi-solid material in a two-phase solvent system. The lower phase is chloroform and the upper aqueous phase contains the DNA. The protein-containing silica is present as an intermediate solid or semi-solid layer which is easily separated away. The cross-linked silica is preferably prepared by cross-linking silica gel with 3-aminopropyltriethoxysilane, followed by reaction with gluteraldehyde to introduce protein-reactive CHO groups.

However, DNA extracted from plants often contains polysaccharides as an impurity, which are not encountered with DNA derived from most other organisms. Such polysaccharides may have enzyme-inhibitory properties, which may subsequently prove troublesome should the DNA be subsequently subjected to enzyme digestion, for example restriction enzyme digestion. To date, most extraction methods have employed the expensive and time-consuming caesium chloride density gradient technique to remove these polysaccharides (Bendich A J, Anderson R S, Ward B L (1980) Plant DNA: long, pure and simple. In: Leaver Cj(ed) Genome Organisation and Expression, pp 31–33. New York: Plenum Press; Murray H G., Thompson W F.(1980) Nucleic Acids Res 8:4321–4325; Taylor B, Powell A (1982) Isolation of plant DNA and RNA. Focus 4:4–6.). Other methods have also been reported (Dellaporta S L, Wood J, Hicks J B (1983) Plant Mol Biol Rep 1:19–21. Zimmer E A, Newton K J (1982) A simple method for the isolation of high molecular weight DNA from individual maize seedlings and tissues. In: Sheridan W F (ed) Maize for Biological Research. Grand Forks, N.D.: University press, University of North Dakota.) however, such techniques are generally only applicable to a limited number of plant species and tissue types. The separation of polysaccharides from nucleic acids by the differential solubilities in the presence of cetyltrimethylammonium bromide has also been reported (Rogers S O, Bendich A J (1988) Plant Mol Biol Manu.A6:1–10.); but this procedure requires organic extraction which may cause some degradation of the DNA.

It is an object of the present invention to provide a convenient process for the isolation of polynucleotides from polysaccharide-containing mixtures.

This and other objects of the present invention will become apparent from the following description and examples.

STATEMENT OF INVENTION

In one aspect, the present invention provides a process for the isolation of polynucleotides from an aqueous mixture containing polynucleotides and polysaccharides, which comprises:

placing the said aqueous mixture in contact with a polymer gel having free —B(OH)$_2$ groups, reactive with the polysaccharides (and is non-reactive to polynucleotides) wherein the polymer gel is capable of forming a solid or semi-solid material containing the polysaccharides; and separating the polynucleotides from said solid or semi-solid polysaccharide-containing material.

DETAILED DESCRIPTION

The polymer gel may be any suitable gel material which is insoluble in the solvents employed. It may be for example a polymerised silica gel, or polyacrylate gel, a polystyrene gel or a polyester gel. The —B(OH)$_2$ groups may be present in the monomer prior to polymerisation, or may be incorporated by reaction with existing groups, such as OH or X, on the polymer.

A preferred polyacrylate is prepared by copolymerisation of dihydroxyborylanilino-substituted methacrylic acid with 1,4-butanediol dimethacrylate and is available from Aldrich Chemical Company.

A preferred polymer gel is a polymerised silica gel. Whilst the —B(OH)$_2$ groups may be attached directly to the polymerised silica gel, it is preferred to modify a CHO containing silica gel produced as described in WO92/05181. This involves reaction of the aldehyde groups on the silica gel with a —B(OH)$_2$ containing amine, for example according to the following simplified scheme.

SCHEME A

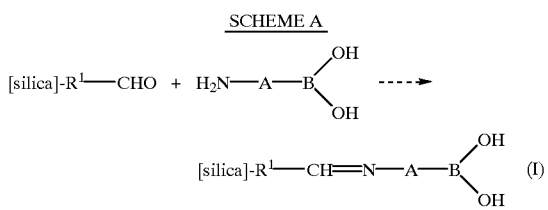

where

R$^1$ is C$_{2-6}$ alkylidene; and

A is independently selected from C$_{2-6}$ alkylidene, a polyether such as

—(CH$_2$CH$_2$O)$_n$—, or an arylene group such as phenylene or napthylene; (n is usually 5 to 100).

The amine may contain one or more amino groups and one or more boric acid —B(OH)$_2$ groups.

During preparation of the boric acid substituted silica gel, the final product is preferably thoroughly washed since the presence of any residual chemical agents may inhibit enzyme-restriction of the extracted DNA. Preferably a pH of substantially neutral is employed.

The cross-linked silica gel containing CHO or CO groups may be produced as described in WO92/05181.

Alternatively, as mentioned above, the boric acid group may be attached directly to the silica, for example according to simplified scheme B.

SCHEME B

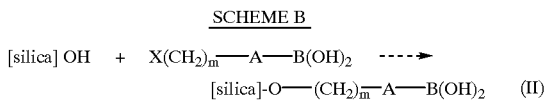

where

X is OH, halo (preferably Cl or Br) or leaving group such as tosylate, mesylate or brosylate;

A is as given above; and m is O to 10.

In a further aspect of the invention there is provided a material for use in the process which comprises a polymerised silica gel having free $B(OH)_2$ groups of general formula (III):

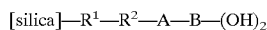
[silica]—$R^1$—$R^2$—A—B—$(OH)_2$ wherein $R^1$ is independently selected from $C_2$–$C_6$ alkylidene or O;

$R^2$ is independently selected from —CH═N, $(CH_2)m$ wherein m is O or a whole integer in the range 1 to 10; and A represents a $C_2$–$C_6$ alkylidene, polyether or arylene.

The invention also relates to a material for use in the process which comprises a polymerised silica gel having free —$B(OH)_2$ groups, especially a material of general formula (I) or (II) above.

The polymerised silica gel material is preferably derived from silica gel of a particle size 250 to 400 mesh.

The resulting boric acid substituted gel is usually solid or semi-solid to facilitate use in separation from the DNA-containing solution. However, reaction of the free —$B(OH)_2$ groups with polysaccharide may also result in a material which, irrespective of its original form, is converted by reaction with the polysaccharide into solid or semi-solid material which can be readily separated from the DNA-containing solution. The boric acid substituted gel reacts with polysaccharide impurities present in plant extracts by a well established mechanism whereby boric acid reacts with 1,2-dihydroxy compounds to yield a cyclic boric acid ester, for example according to Scheme C.

SCHEME C

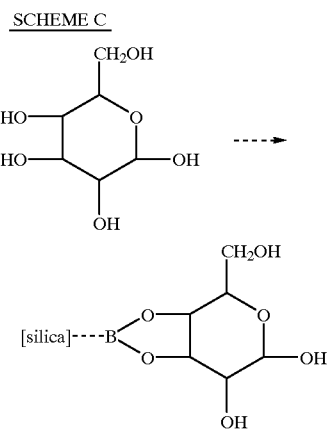

Preferably, the solid or semi-solid material containing absorbed polysaccharide has a density different from the DNA-containing solution. In a preferred embodiment, isolation of DNA is achieved in a two-phase solvent extraction system, wherein the aqueous DNA solution is present as the upper layer. In this case the density of the gel material containing absorbed polysaccharide is preferably arranged such that it forms an intermediate layer between the upper aqueous layer and the lower solvent layer, so as to assist complete removal of the aqueous DNA-containing layer without contamination from the solvent layer.

Preferably, the gel forms a solid mass (e.g. a disc) at the interface, which is easily removable.

The technique of the present invention is applicable to the separation of oligonucleotides in general (such as DNA and RNA) from polysaccharide-containing aqueous mixtures.

If necessary, the present technique for the removal of polysaccharide impurities may be carried out prior to or subsequent to the removal of any protein impurities in a manner described in WO92/05181.

The preferred embodiment allows the isolation of DNA to be carried out speedily and with a high yield and improved purity.

Embodiments of the present invention will now be described by way of example only.

EXAMPLE 1

Preparation of Polymerised Silica Gel 50 grams of dried particulate silica gel (250–400 mesh) was activated by addition of 300 mL of 5% nitric acid. One hour later the silica gel was washed with 1000 mL of double distilled water and then 400 mL of HPLC grade methanol using a vacuum pump.

The pH value of 300 mL of 10% 3-aminopropyltriethoxysilane $(C_2H_5O)_3$—Si—$CH_2CH_2CH_2NH_2$ (APTES) was adjusted to 3.5 with 6N hydrochloric acid. The solution was then added to the above silica gel. The reactants were put in a 75° C. water bath for 2 hours and then washed with 500 mL of double distilled water. The treated silica gel was then dried in a 115° C. oven for at least 5 hours.

The pH value of 400 mL aqueous glutaraldehyde OHC—$(CH_2)_3$—CHO (2.5%) was adjusted to 7.0 and the solution was then added to the treated silica gel. The reaction was allowed to proceed at room temperature for 2 hours with stirring. The resulting polymerised silica gel was then thoroughly washed with 1000 mL of deionised double distilled water, and then drained using a vacuum pump, to yield a free-flowing powder.

EXAMPLE 2

Preparation of —$B(OH)_2$ Substituted Silica Gel 30 mg of 3-aminophenylboronic acid monohydrate (pH 7) was dissolved in 2 ml of ethanol and 1.3 g of dried polymerised silica gel (PSG) was suspended in this solution. The preparation of this PSG, whose surface is covered in free aldehyde groups, is described in Example 1 and WO92/05181. The mixture was mixed with a magnetic stirrer at 50° C. for 3 hours, and then kept at room temperature overnight. The reaction was allowed to proceed under neutral conditions.

The product was centrifuged at 700 XG for 3 minutes and the centrifugate transferred into a 50 ml test tube. To the tube was added 50 ml of double distilled water and the mixture gently stirred with a spatula and by gently inverting the tube for 15 seconds. The mixture was again centrifuged at 700 XG for 3 minutes, and the supernatant discarded. The process was repeated four times with doubled distilled water (total 200 ml) and two times with 1 X TE buffer (pH 7) (total 100 ml) to achieve thorough washing of the product.

The —$B(OH)_2$ substituted PSG was spread onto a flat glass plate and placed in a 56° C. incubator for 5–10 minutes before storage in a sealed tube.

EXAMPLE 3

Measurement of Glucose as a Standard

Method: phenol-sulphuric acid calorimetric assay

Sensitivity: –1–60 ug glucose in 200 ul (–3 uM–2 mM)

Final volume: 1.4 ml
Microanalytical cuvette: 1 ml
Control solution: 1 X TE buffer (10 mM Tris hydrochloride and 1 mM EDTA adjusted to desired pH with 1M NaOH)
Reagents:
(A) 0.25 g phenol dissolved in 5 ml of 1 X T E buffer (5% w/v).
(B) Concentrated sulphuric acid.
(i) Preparation of Glucose Standard Curve A 2 mM of glucose solution containing 0.4 mg of glucose in 100 ml of 1 X TE buffer was prepared and maintained at 4° C. Various volumes of this solution (150, 100, 75, 50, 25, 10 and 0ul) were diluted to a volume of 200 ul respectively with 1 X TE buffer in a 2 ml tube and then to each solution was added 200 ul of reagent A immediately followed by 1.0 ml of reagent B, care being taken not to touch the sides of the tube. The undisturbed mixtures were left at ambient temperature for 10 minutes before shaking vigorously for 1 minute. After 30 minutes the absorbances of each glucose standard solution was recorded at 490 nm using a 1.0 ml microanalytical cuvette. A simultaneous blank sample which contained IX TE buffer solution in place of the glucose was used as a control to calibrate the measured data. A standard curve was constructed from the absorbance at 490 nm against concentration in millimole for each standard glucose solution. The curve showed linearity (r=0.999) and was represented by the regressive equation.

$$Y = 1.569616 X + 0.021081.$$

where Y is absorbance at 490 nm and X is the concentration of glucose in mM.

(ii) Assessment of the Binding Power of Substituted PSG Using Glucose as a Model Compound To a series of 200 ul aliquots of 1 mM glucose in 1 X TE buffer was added 0, 50, 100, 150 and 200 mg of —$B(OH)_2$ substituted PSG (Table 1). A series of blanks were prepared by adding the same weight of non-substituted PSG to 200 ul of 1 X TE buffer. The mixtures were gently shaken on a tilt shaker at room temperature for 20 minutes and then spun at 1,300 X G for 3 minutes. The supernatants were transferred to a series of 2-ml tubes and the volume of each sample was diluted to exactly 200 ul with 1 X TE buffer. Each sample was mixed with reagent A (200 ul), followed immediately by reagent B (1 ml). The undisturbed mixtures were left at room temperature for 10 minutes before shaking vigorously for 1 minute. The absorbance of each sample was recorded at 490 nm after a further 30 minutes using a 1 ml microanalytical cuvette. The quantity of glucose remaining in solution after addition of the —$B(OH)_2$ substituted PSG was calculated from the recorded $A_{490}$ values using the regression equation for the standard glucose curve. This experiment was repeated.

A 1 mM solution of glucose was employed for this test rather than a 2 mM solution in order restrict the absorbance range.

The results (Table 1) show that the substituted PSG was effective in removing carbohydrates from solution.

It can be seen that the glucose remaining decreases as the amount of substituted PSG increases. Using 50 mg to 200 mg of dried substituted PSG 47% to 82% of the glucose was removed from a 1 mM glucose solution in 1 X TE buffer. The amount of glucose bound by the PSG is approximately linear over the range 0.2 to 6.0 mM corresponding to the addition of 50 mg of PSG (r=0.9939).

EXAMPLE 4

Extraction of Corn Plant DNA Using —$B(OH)_2$ Substituted PSG

Two portions, 0.5 g, of frozen corn (-20° C.) were ground together with two to three times their volumes of dry ice to yield a free flowing powder. Each corn sample (0.5 g and 5 g) with its dry ice was transferred to separate test tubes of 2 and 15 ml capacity respectively and then kept under ambient conditions for 5–10 minutes until the samples had melted. To the tubes were added respectively, lysis buffer (400 ul and 4 ml) and 5 M sodium perchlorate (150 ul and 1.5 ml). The mixtures were firstly mixed at room temperature on a tilt shaker for 20 minutes and then at 65° C. for a further incubation time of 20 minutes with gentle mixing every 5 minutes. The final mixtures were cooled to ambient temperature. This treatment causes lysis of the cells, denaturing and partial digestion of any protein. Volumes (500 ul and 5 ml) of chloroform (-20° C.) were added to the lysis mixtures which were then subjected to shaking at room temperature on a tilt shaker for 10 minutes. The mixtures were centrifuged at 1,300 X G for 3 minutes. Aliquots of 100 ul and 700 ul of new PSG slurry (25 mg new PSG in 30 ul 1 X TE buffer) were added to each tube with mixing on a tilt shaker for 20 minutes and then the contents spun at 1,300 XG for 3 minutes in a swinging-bucket head centrifuge. The top aqueous phase in each tube was poured into a fresh tube (2 ml and 15 ml) respectively and two equal volumes of ethanol at 4° C. was added to each tube which was then inverted until the DNA precipitated. The DNA mass in each tube was transferred to a 15 ml volume tube with a sterile glass rod. Each pellet was finally redissolved in 3-ml and 20 ml of 1 X TE buffer respectively (Table 2).

To obtain the quantity and purity of the extracted corn plant DNA from corn using the PSG—$B(OH)_2$, the absorbance of each sample was determined at 260 and 280 nm. The yield and the $A_{260}/A_{280}$ ratio of each sample was calculated from the values of measured absorbance.

From Table 2 it can be seen that using the PSG—$B(OH)_2$ to extract plant DNA from 0.5 g and 5 g corn, the yields were 126 and 882 ug respectively. The average $A_{260}/A_{280}$ was 1.81 suggesting that protein free DNA has been extracted (Maniatis T. Fritsch E F and Sambrook J (1982), Molecular Cloning: A Laboratory Manual, Cold Spring Harbor Laboratory, Cold Spring Harbor, N.Y., PP 458–460).

TABLE 1

Variation in the amounts of glucose removed from a standard solution by various amounts of -$B(OH)_2$ substituted PSG.

| Samples No | 0 | 1 | 2 | 3 | 4 |
|---|---|---|---|---|---|
| PSG-$B(OH)_2$ mg | 0 | 50 | 100 | 150 | 200 |
| 1 mM Glucose ul | 200 | 200 | 200 | 200 | 200 |
| Reagent A ul | 200 | 200 | 200 | 200 | 200 |
| Reagent B ml | 1 | 1 | 1 | 1 | 1 |
| $A_{490}$ | 1.605 | 0.848 | 0.651 | 0.435 | 0.306 |
| Glucose remaining mM | 1.0 | 0.53 | 0.40 | 0.26 | 0.18 |

TABLE 2

Extraction of DNA from corn using -B(OH)₂ substituted PSG.

| Samples (g) | $A^{260}$ | $A_{280}$ | $A_{260}/A_{280}$ | Yield (ug) |
|---|---|---|---|---|
| 5 | 0.882 | 0.514 | 1.72 | 882 |
| 0.5 | 0.839 | 0.439 | 1.91 | 126 |

We claim:

1. A process for the isolation of polynucleotides from an aqueous mixture containing polynucleotides and polysaccharides, which comprises:
   a) placing the said aqueous mixture in contact with a polymer gel having free —B(OH)₂ groups which are reactive with the polysaccharides and substantially non-reactive with the polynucleotides, wherein upon reaction with the polysaccharide the polymer gel forms a solid or semi-solid material containing the polysaccharides; and
   b) separating the polynucleotides from said solid or semi-solid polysaccharide material by centrifugation on the basis of said solid or semi-solid polysaccharide-containing material having a density different from the polynucleotide-containing solution.

2. A process according to claim 1 wherein the —B(OH)₂ containing polymer gel is selected from the group consisting of polymerized silica gel, polyacrylate gel, polystyrene gel and polyester gel.

3. A process according to claim 2 wherein the —B(OH)₂ containing polymer gel is of a compound of general formula III:

[silica]—R¹—R²—A—B(OH)₂ wherein
R¹ is independently selected from C₂–C₆ alkylidene or O;
R² is independently selected from —CH=N, or (CH₂)m where
m is O or a whole integer in the range from 1 to 10; and
A represents a C₂–C₆ alkylidene, a polyether or arylene.

4. A process according to claim 1 wherein the polymer gel is of a compound of general formula I:

[silica]—R¹—CH=N—A—B(OH)₂ wherein
R¹ is C₂–C₆ alkylidene; and
A is independently selected from C₂–C₆ alkylidene, a polyether or arylene.

5. A process according to claim 1 wherein the polymer gel is of a compound of general formula II:

[silica]—O—(CH₂)m—A—B(OH)₂ wherein
A represents C₂–C₆ alkylidene, a polyether or arylene; and
m is O or a whole integer in the range from 1 to 10.

6. A process according to any one of claims 3 to 5 wherein A is selected from C₂–C₆ alkylidene, (CH₂CH₂O)n, and napthylene, and n is a whole integer in the range from 5 to 100.

7. A process according to claim 1 wherein the —B(OH)₂ containing polymer gel is selected from solid and semi-solid gels.

8. A process according to claim 1 wherein isolation of DNA is achieved in a two-phase solvent extraction system wherein the aqueous mixture containing polynucleotides is present as the upper layer.

9. A process according to claim 1 wherein the polynucleotides to be isolated are derived from plants.

10. A process for the isolation of RNA from an aqueous mixture containing RNA and polysaccharides, which comprises:
    a) placing said aqueous mixture in contact with a polymer gel having free —B(OH)₂ groups which are reactive with the polysaccharides, wherein upon reaction with polysaccharide, the polymer gel forms a solid or semi-solid material containing the polysaccharides; and
    b) separating the RNA from said solid or semi-solid polysaccharide-containing material.

11. A process according to claim 10 wherein the —B(OH)₂ containing polymer gel is of a compound of general formula III:

[silica]—R¹—R²—A—B(OH)₂ wherein
R¹ is independently selected from C₂–C₆ alkylidene or O;
R² is independently selected from —CH=N, or (CH₂)m where m is 0 or a whole integer in the range from 1 to 10; and A represents a C₂–C₆ alkylidene, a polyether or arylene.

12. A process according to claim 11 wherein the polymer gel is of a compound of general formula I:

[silica]—R¹—CH=N—A—B(OH)₂ wherein
R¹ is C₂–C₆ alkylidene; and
A is independently selected from C₂–C₆ alkylidene, a polyether or arylene.

13. A process according to claim 11 wherein the polymer gel of a compound of general formula II:

[silica]—O—(CH₂)m—A—B(OH)₂ wherein
A represents C₂–C₆ alkylidene, a polyether or arylene; and
m is 0 or a whole integer in the range from 1 to 10.

14. A process according to claim 10 wherein A represents C₂–C₆ alkylidene or (CH₂CH₂O)n or phenylene or napthylene and n is a whole integer in the range from 5 to 100.

15. A process according to claim 11 wherein the boric acid substituted gel is solid or semi-solid.

16. A process according to claim 10 wherein the isolation of RNA is achieved in a two-phase solvent extraction system wherein the aqueous RNA isolation is present as the upper layer.

17. A process according to claim 10 wherein the RNA to be isolated is derived from plants.

* * * * *